United States Patent
Gibbs

[11] Patent Number: 5,734,464
[45] Date of Patent: Mar. 31, 1998

[54] RED BLOOD CELL SPILLOVER DETECTION TECHNIQUE

[75] Inventor: Bruce W. Gibbs, Arvada, Colo.

[73] Assignee: Cobe Laboratories, Inc., Lakewood, Colo.

[21] Appl. No.: 746,109

[22] Filed: Nov. 6, 1996

[51] Int. Cl.⁶ .................................................. G01N 33/48
[52] U.S. Cl. ............................................................ 356/39
[58] Field of Search ........................ 356/39–42; 128/633

[56] References Cited

U.S. PATENT DOCUMENTS

| | | |
|---|---|---|
| Re. 29,141 | 2/1977 | Hogg . |
| 3,236,602 | 2/1966 | Isreeli . |
| 3,527,542 | 9/1970 | Penhasi et al. . |
| 4,227,814 | 10/1980 | Soodak et al. . |
| 4,229,179 | 10/1980 | Lee . |
| 4,444,498 | 4/1984 | Heinemann . |
| 4,522,494 | 6/1985 | Bonner . |
| 4,577,964 | 3/1986 | Hansen, Jr. . |
| 4,745,279 | 5/1988 | Karkar et al. . |
| 4,810,090 | 3/1989 | Boucher et al. ................... 356/39 |
| 4,834,890 | 5/1989 | Brown et al. . |
| 5,141,303 | 8/1992 | Yamamoto et al. ............. 128/666 |
| 5,372,136 | 12/1994 | Steuer et al. . |
| 5,437,598 | 8/1995 | Antwiler . |

*Primary Examiner*—Frank G. Font
*Assistant Examiner*—Amanda Merlino
*Attorney, Agent, or Firm*—Carol W. Burton, Esq.; Francis A. Sirr, Esq.; Holland & Hart LLP

[57] ABSTRACT

An apparatus and a method are provided to monitor a generally transparent blood tube at a location that is downstream from a blood separator in order to detect the presence of red blood cells in a tube that is intended to carry a different blood component, for example platelets. A red light source and a green light source are located in relation to the tube so that red light emission and green light emission are directed toward the tube and toward the flowing blood component(s) that is carried within the tube. The red light source produces a red reflection intensity from red blood cells whose magnitude increases as a function of an increase in the concentration of red blood cells. The green light source produces a green reflection intensity from the red blood cells whose magnitude decreases as a function of an increase in the concentration of the red blood cells. These two light reflections are sensed by means of one broadband photodetector, or by two band-specific photodetectors, that are located on the same side of the tube, so as to be responsive only to reflected light. An output is provided by detecting the ratio of the magnitude of the red reflection intensity to the magnitude of the green reflection intensity.

21 Claims, 8 Drawing Sheets

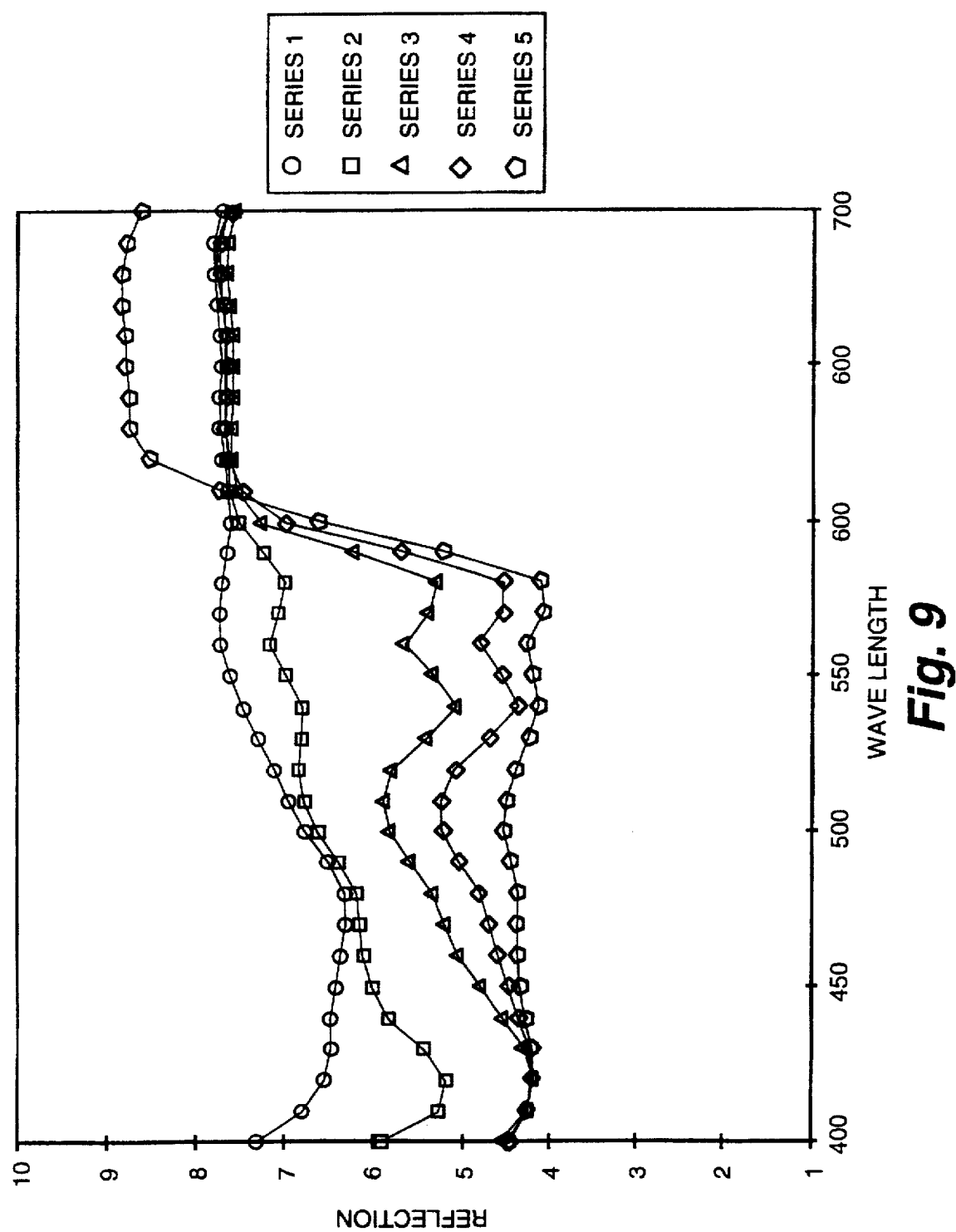

RED BLOOD CELL SPILLOVER DETECTION TECHNIQUE

1. FIELD OF THE INVENTION

The present invention generally relates to the field of blood separation, and specifically to the separation of whole human blood into its red blood cell, plasma and platelet components. More particularly, the present invention relates to the detection of an undesirable spillover of red blood cells into a blood component stream, for example a platelet stream, that should not contain red blood cells.

2. BACKGROUND OF THE INVENTION

Continuous blood separators are used to separate whole human blood into its various components, such as platelets, red blood cells and/or plasma. These components are removed from the separators in separate streams, sometimes referred to as collect tubes. Normally, the collect tubes of the blood separator are continuously monitored to detect the undesirable occurrence of a spillover of one blood component into a collect tube intended to carry a different blood component. For example, the spillover of red blood cells into a collect tube intended to carry only platelets may be monitored.

A conventional technique by which undesirable spillover of red blood cells is monitored is the measurement of a color index of a non-red blood cell blood component that flows through a collect tube. This measurement is taken at a point downstream of the blood separator. By using a green light source and measuring the optical density of the non-red blood cell blood component, the total number of particles in the flowing non-red blood cell blood component and the green light absorbence of the non-red blood cell blood component can be monitored. An increase in green light absorbence in relation to optical density is then correlated to the occurrence of a red blood cell spillover.

This type of detection equipment typically requires a light source to be physically positioned on one side of a collect tube and a photosensor located on the opposite side of the collect tube. For this system to work in an optically efficient manner, the portion of the collect tube adjacent the light source must present a generally flat surface to the light source and the photosensor. Relatively expensive schemes and custom containers have been used to produce a flat interface to the light source and to the photosensor, to thereby increase optical efficiency in this manner. For example, collect tubes may be flattened.

Another problem experienced with such detection equipment is that measurement of optical density requires measurement of the intensity of light that is received by the photosensor. Artifacts such as dirt particles that affect the light intensity received by the photosensor tend to provide a false indication of red blood cell spillover. In addition, there remains a continuous need for a detector equipment capable of greater sensitivity in a sensitive detection of red blood cell spillover.

The following United States patents are of general interest: U.S. Pat. No. 3,236,602 relates to a flow cell for the colorimetric examination of the light transmission characteristics of a liquid. U.S. Pat. No. 3,527,542 relates to apparatus for measuring blood flow wherein a first beam of monochromatic light passes through a cuvette to impinge on a first photocell while a second light beam impinges on a second photocell. The two photocell outputs are then compared. Reissue U.S. Pat. No. 29,141 describes a slit cell for use with optical particle sensors that operate on the principle of light scattering or interception.

Various patents identify light sources having particular wave lengths for the measurement of liquid characteristics. U.S. Pat. No. 4,227,814 describes an optical detector that is used with blood separating apparatus wherein red blood cell spillover is detected as a function of optical density. Low power light (750 foot candles at a power consumption of 1 to 2 watts) passes through the sample and a photodetector senses the optical density of the sample. Blue-green light 550 nanometers (nm) wavelength and a type 9 CAD sulfide photodetector are used. U.S. Pat. No. 4,229,179 describes spectrophotometric measuring apparatus wherein the visible, UV or fluorescent radiant energy that passes through a sample is detected. U.S. Pat. No. 4,444,498 describes the measurement of blood characteristics by using blood reflected light provided by two intermittently operating light sources having two different wavelengths (red and infrared). Optical feedback loops control the intensity of the two light sources. A flat-bandwidth sensor detects the two reflections of different wavelengths.

Also by way of example, U.S. Pat. No. 4,810,090 describes the sensing of platelet concentration, and the detection of red blood cell spillover into the platelet flow, by using an infra-red-emitting LED (875 nm) and a green-emitting LED (565 nm) that operate at different times. These two LEDs emit light along an axis that extends through the stream of platelet flow. A first light sensor is placed on-axis and opposite the two light sources to detect light that passes on-axis and through the platelet stream. A second light sensor is placed generally across from the two light sources, but is located upstream of the first sensor, so as to measure light that is scattered off-axis and upstream of the two light sources. A third light sensor is placed generally across from the two light sources but is located downstream of the first sensor, to measure light that is scattered off-axis and downstream of the light sources. Under abnormal conditions, for example, when clumping, air bubbles, hemolysis, and spillovers of red blood cells or white blood cells has occurred, a color-index and a scatter-index are calculated.

Scattered light is also measured as a means of identifying blood components in other U.S. Patents. For example, U.S. Pat. No. 4,522,494 describes an apparatus that determines the concentration of non-aggressive platelets and the concentration of discs that are within a flexible bag, using scattered laser light. U.S. Pat. No. 4,577,964 relates to the use of scattered light to discriminate platelets from red blood cells within a sample volume. U.S. Pat. No. 4,745,279 relates to the diffusion of infrared light by a volume of blood in order to measure the hematocrit of a volume of blood. This device may be used to measure oxygen saturation by the use of an LED light emitter and a reflection detector that are located on the same side of the blood volume. U.S. Pat. No. 5,372,136 describes a finger-clip/ear-lobe-clip arrangement in which at least two wavelengths of light are passed through body tissue and light transmission or reflection is detected by a photodetector.

While the prior art as exemplified above is generally useful for its limited intended purposes, the need remains for a construction and arrangement that provides a more sensitive detection of red blood cell spillover. In addition, there remains a need for equipment configuration wherein collect tubing does not have to be of special flattened construction manually between opposing transmitted and receiving devices.

SUMMARY OF THE INVENTION

The present invention provides a new, unusual and unobvious construction and arrangement for monitoring the undesirable spillover of a blood component in a tube intended to carry a different blood component. The present invention is particularly adapted for continuously monitoring one or more blood collect tubes at one or more locations downstream of a continuous blood separator, to detect the undesirable spillover of one blood component into a collect tube intended to carry a different blood component. In an embodiment of the invention, the undesirable spillover of red blood cells into a tube intended to carry platelets is continuously monitored.

In accordance within its broader aspects, the present invention provides two light sources having two different but related emission wavelengths. The light outputs of these two light sources are directed toward a tube intended to exclusively carry a first blood component. The two different light wavelengths are selected such that (1) the first light source has a first wavelength which is reflected from a second blood component with an intensity that increases with an increase in the concentration of the second blood component, and (2) the second light source has a second wavelength which is reflected from the second blood component with an intensity that decreases as a function of an increase in the concentration of the second blood component.

In accordance with the present invention, the intensity of the first light source's reflection and the intensity of the second light source's reflection are both detected. This results in an intensity-1 electrical signal that increases when the second blood component concentration or density increases, and an intensity-2 electrical signal that decreases when the second blood component concentration or density increases. By electrically comparing the intensity-1 signal to the intensity-2 signal, an arrangement is provided which is very sensitive to the occurrence of a spillover of the second blood component into the tube intended to carry only the first blood component. Preferably this comparison comprises a ratio measurement wherein the numerator increases and the denominator decreases as the concentration of red blood cells increases.

In one embodiment of the present invention, the second blood component comprises red blood cells, the first light source is a red light source, the second light source is a green light source, and the electrical comparison operates to detect the ratio of the reflected red light intensity to the reflected green light intensity. Since an increase in the concentration of red blood cells causes the numerator of this ratio to increase, as the denominator of this ratio concomitantly decreases, the resulting ratio signal is very sensitive to changes in the concentration of red blood cells within the tube. For example, this ratio changes markedly at hematocrit of 1%, 0.5% and even below 0.5%, thus making the apparatus/method of this invention more sensitive than prior detection of red blood cell spillover.

The light outputs of these two light sources may be continuous, in which case the two light reflections are simultaneously detected by the use of two light specific detectors that are individually responsive only to one of the two wavelengths. Alternatively, the two light sources are pulse-energized during two different time intervals, and one or two light detectors are provided, having a relatively wide wavelength response. Since the two light reflections occur during two different time intervals, interference between the two light reflections is prevented.

Alternatively, when the second blood component includes another particular component, reflection of the green and red light from that particular component is found to be affected in a similar manner as the concentration or density of the component changes.

In an embodiment of the present invention, each light source and its mating light detector are physically mounted on the same side of the tube. Preferably, the two light sources and the two detectors are physically located on the same side of the tube. In this configuration the tube can be automatically loaded into the apparatus of this invention, and set-up time and manufacturing cost are minimized. Moreover, the construction and arrangement of this invention does not require the use of cuvettes, does not require that the tube be flattened, is less prone to the false detection of red blood cell spillover, locates the light emitters and the light detectors on the same side of the tube, and provides for the optically efficient and sensitive detection of red blood cell spillover.

These and other objects, advantages and features of the present invention will be apparent to those of skill in the art upon reference to the following detailed description of presently preferred embodiments of the invention, the drawings and the appended claims.

BRIEF DESCRIPTION OF THE DRAWING

FIG. 9 is a graph which contains a multiplicity of curves similar to that of FIGS. 7 and 8, in which the blood sample is from a donor having a relatively low concentration of platelets.

DETAILED DESCRIPTION OF THE INVENTION

Figure 1:
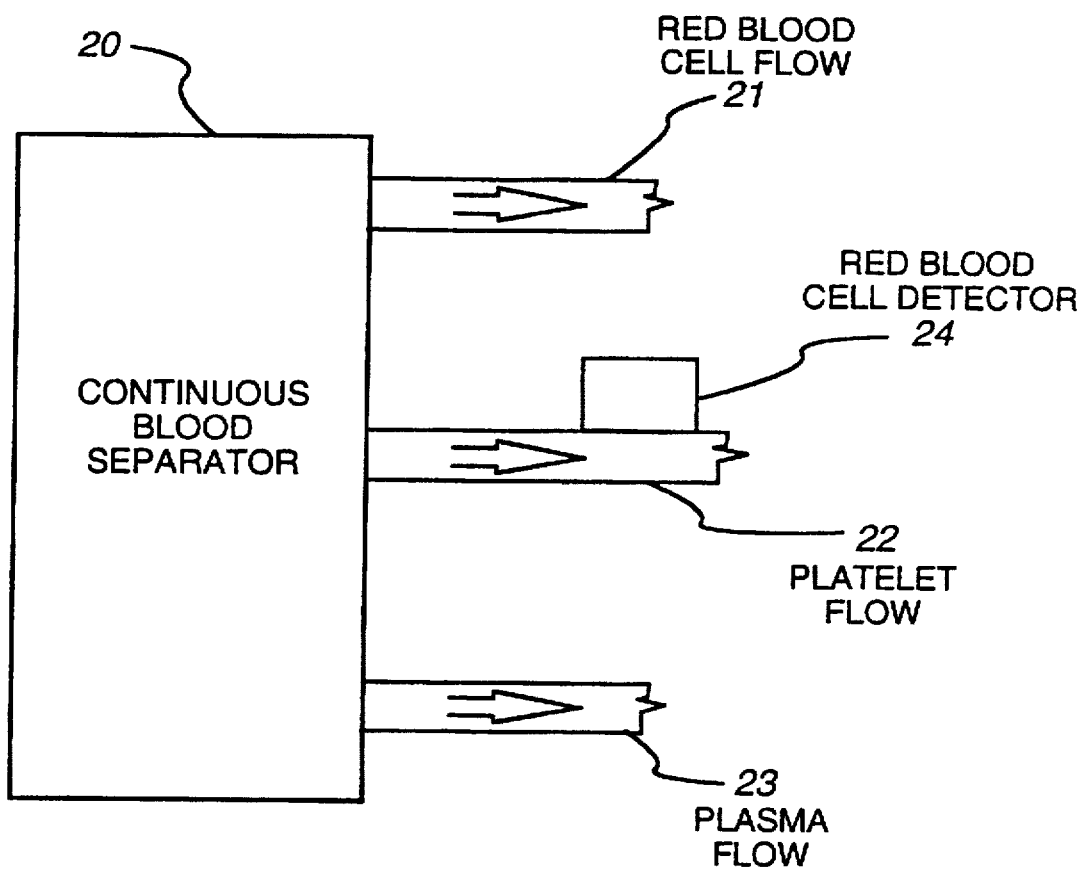
FIG. 1 is a schematic representation of a continuous blood separator having three relatively transparent blood component collect tubes and a red blood cell detector in accordance with the present invention associated with one of the collect tubes.

As shown in FIG. 1, conventional continuous blood separator 20 includes three relatively transparent blood component collect tubes 21, 22 and 23. Collect tube 21 is intended to carry red blood cells. Platelet collect tube 22 is intended to carry platelets, with the flow rate of the blood component within collect tube 22 typically in the range of from about 0.8 to about 25 ml/min. Plasma collect tube 23 is intended to carry blood plasma. In FIG. 1 the direction of blood component flow is from left to right, as is shown by the arrows associated with collect tubes 21, 22 and 23, with it being assumed that the blood being separated by separator 10 is human blood, but this selection is by way of example only. In this embodiment, collect tubes 21, 22 and 23 are constructed of optically transparent polyvinylchloride and are generally circular in cross section, and having an inner diameter of about 2.87 mm and an outer diameter of about 4.75 mm.

A red blood cell spillover detector 24 of the present invention is associated with collect tube 22. While the physical spacing or distance that exists between detector 24 and separator 20 is not critical, a utility of the present invention includes halting separator 20 when red blood cells are detected in platelet collect tube 22. Therefore, it may be desirable to keep the physical separation between detector 24 and separator 20 at a minimum. In any case, the detector 24 includes light sources and mating light detector(s). In accordance with an important feature of the invention, both light sources and the mating light detector(s) that are within detector 24 are located on the same side of collect tube 22.

Figure 2:
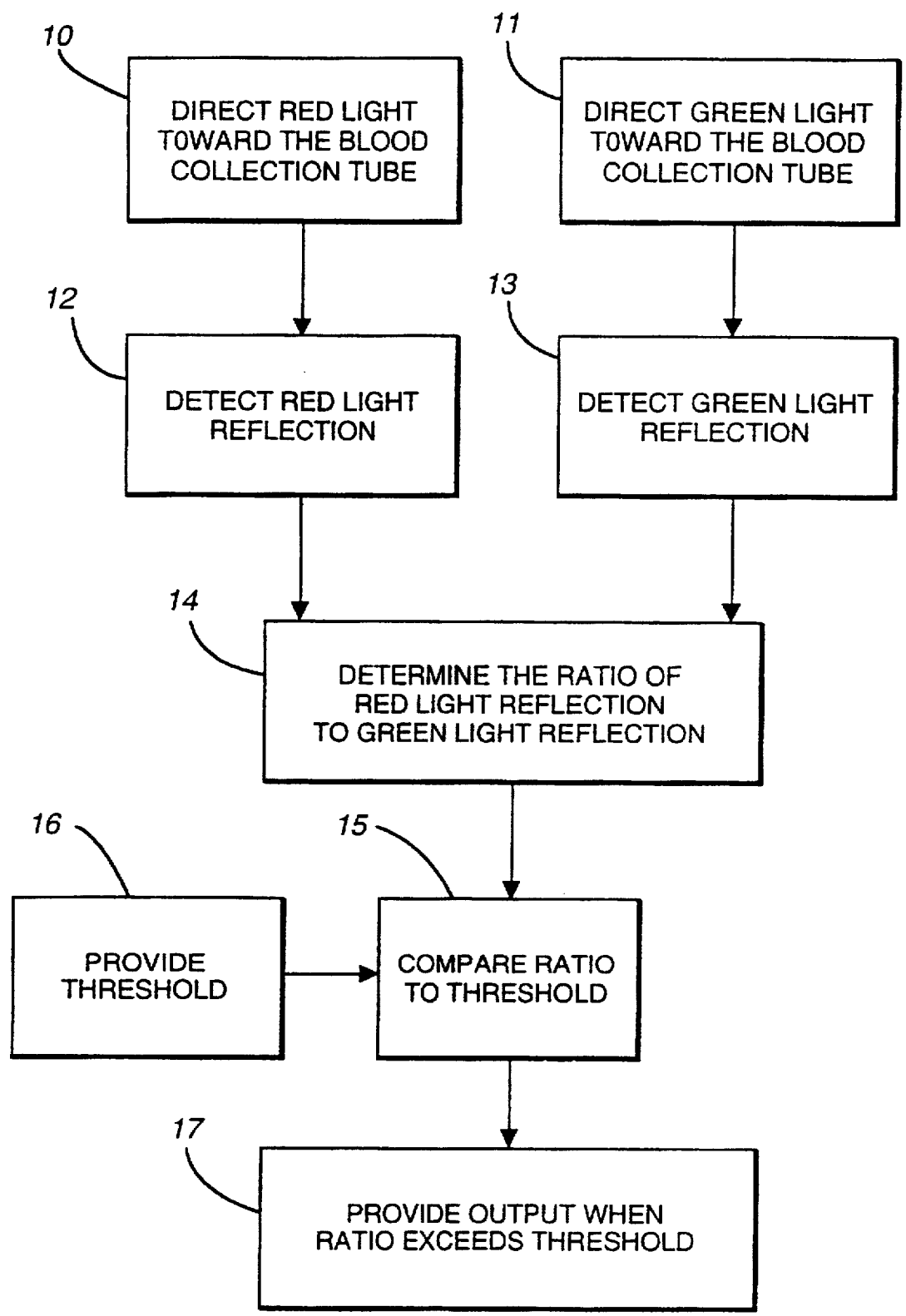
FIG. 2 is a flowchart illustrating the method of the present invention.

FIG. 2 is a flowchart illustrating the present invention. As shown at functions 10 and 11, red light and green light are directed toward the blood collect tube that is to be monitored for the presence or spillover of red blood cells. As used herein, the term green light is intended to mean visible electromagnetic radiation having a wavelength of from about 4,912 to about 5,750 angstroms, and the term red light is intended to mean visible electromagnetic radiation having a wavelength of from about 6,470 to about 7,000 angstroms.

Functions/method steps 10, 11 can occur during the same time interval, in which case two light sensors or light detectors are provided, one sensor being selectively responsive only to red light reflection and the other sensor being selectively responsive only to green light reflection. However, in a preferred embodiment, the two steps 10, 11 occur during two different but closely spaced time intervals. In this embodiment, only one sensor may be provided, this one sensor having a wide wavelength response so that it is responsive to red light reflection during one time interval, and is responsive to green light reflection during another time interval. In any case, the detection of red light reflection and green light reflection are shown at functions 12 and 13, respectively.

At function 14 the magnitude of the red light reflection and the magnitude of the green light reflection are compared. In a preferred embodiment, the ratio of red light reflection magnitude to green light reflection magnitude is determined. While function 14 may be constructed and arranged to directly provide an output, FIG. 2 shows a compare function 15 that compares the ratio that was determined by function 14 to a user supplied threshold value 16, which is the minimum spillover tolerated or lacking in adverse consequences for a given application. A function 17 then responds to comparison 15, and provides an output when the ratio output of 14 exceeds the threshold output of 16.

Figure 3:
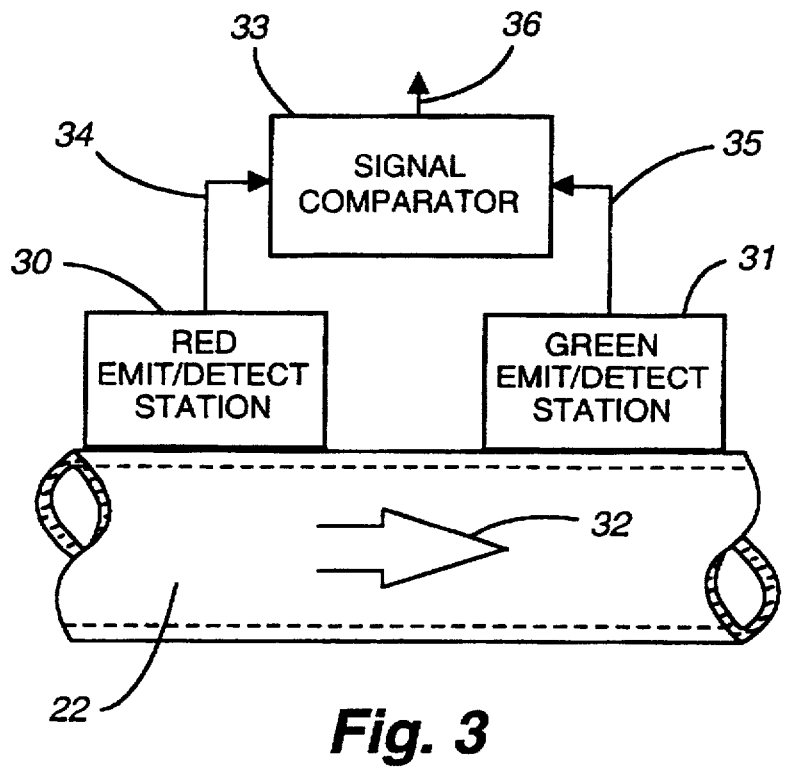
FIG. 3 shows an embodiment of the invention wherein a platelet collect tube has associated therewith a first emit/detect station that operates to emit a first color of light (red) into the collect tube, and then to detect the reflection of this first color from the blood component flow within collect tube, and a second emit/detect station that operates to emit a second color of light (green) into the collect tube, and then to detect the reflection of this second color from the blood component flow within the collect tube.

FIG. 3 shows an embodiment of the invention wherein platelet collect tube 22 has associated therewith a first emit/detect station 30 in accordance with the invention that operates to emit a first color of light (red) into collect tube 22, and then to detect the reflection of this first color from the blood component flow 32 within collect tube 22. Spaced a short distance from station 30 is a second emit/detect station 31 in accordance with the invention that operates to emit a second color of light (green) into collect tube 22, and then to detect the reflection of this second color from the blood component flow 32 within collect tube 22. Note that in accordance with an important feature of the invention, both the light source and its mating light detector are located on the same side of collect tube 22.

The two respective output conductors 34 and 35 of stations 30 and 31 carry electrical signals whose magnitudes are directly proportional to the magnitude of the reflected first light and to the magnitude of the reflected second light. An electrical signal comparator 33 in accordance with the invention operates to compare the two signals on conductors 34, 35, and to provide an output 34 as a result of this comparison.

The two stations 30, 31 may operate during the same time interval having a duration of, for example, fractions of a second. In this case the two signals on conductors 34 and 35 also appear during this common time interval. Signal comparator 33 may or may not include a latch means (not shown) that operates to latch the magnitudes of these two signals 34, 35 to enable a magnitude comparison to be made.

In accordance with an important feature of this invention, the above described signal comparison is a comparison, such as a ratio calculation, that takes advantage of the fact that red light reflection increases and green light reflection decreases as the concentration of red blood cells increases.

The two stations 30, 31 may also operate during two different time intervals that are spaced from one another. In this case, the two signals on conductors 34 and 35 also appear during these two different time intervals, and signal comparator includes a latch means (not shown) that operates to latch the magnitudes of these two signals 34, 35 in order to enable a magnitude comparison to be made after expiration of the later or second of the two time intervals.

While the physical spacing of the two stations 30, 31 along the length of collect tube 22 is not critical to the invention, it may be desirable to maintain this spacing to a minimum, and/or to time the later operation of station 31, relative to the earlier operation of station 30, as a function of the flow rate of the blood component 32 that is within collect tube 22. In this way, both station 30 and station 31 operate on the same flowing volume of blood component 32.

Figure 4:
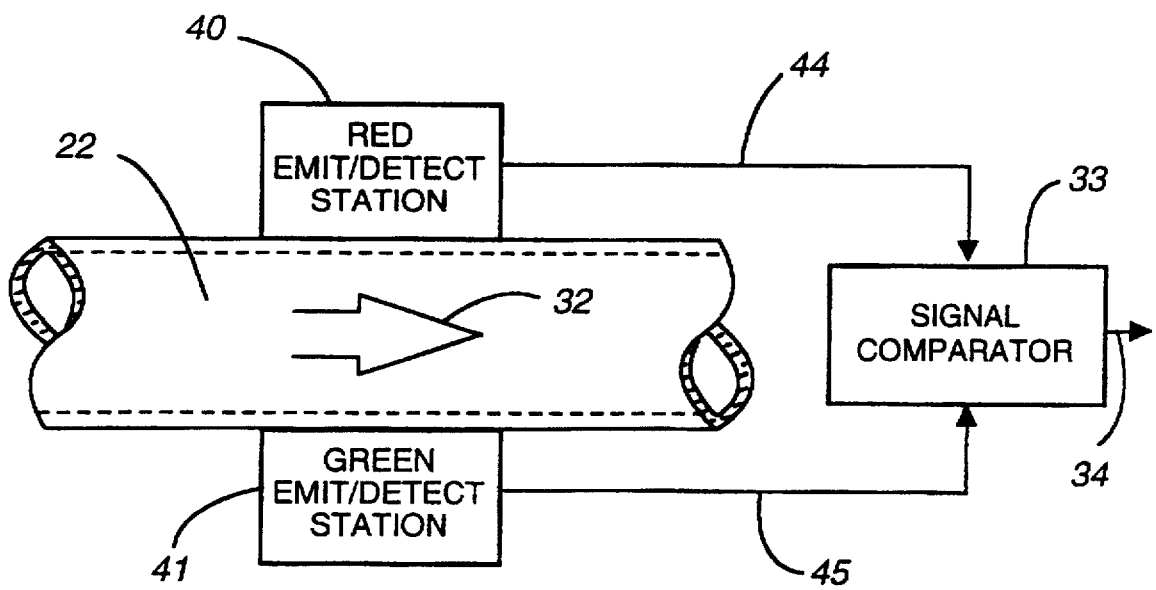
FIG. 4 shows an embodiment of the invention wherein a platelet collect tube has associated therewith a first emit/detect station that operates to emit a first color of light (red) into the collect tube, and to then detect the reflection of this first color from the blood component flow within the collect tube, wherein a second emit/detect station is located diametrically across from the first emit/detect station and is operative to emit a second color of light (green) into the collect tube, and then to detect the reflection of this second color from the blood component flow within the collect tube.

FIG. 4 shows an embodiment of the invention wherein platelet collect tube 22 has associated therewith a first emit/detect station 40 in accordance with the invention that operates to emit a first color of light (red) into collect tube 22, and to then detect the reflection of this first color from the blood component flow 32 within collect tube 22. Located diametrically across from station 40 is a second emit/detect station 41 in accordance with the invention that operates to emit a second color of light (green) into collect tube 22, and then to detect the reflection of this second color from the blood component flow 32 within collect tube 22.

Two respective output conductors 44 and 45 of stations 40 and 41 carry electrical signals whose magnitudes are directly proportional to the magnitude of the reflected first light and to the magnitude of the reflected second light. An electrical signal comparator 33 in accordance with the invention operates to compare the two signals on conductors 44, 45, and to provide an output 34 as a result of this comparison.

The two stations 40, 41 may operate during the same time interval, whereupon the two stations 40, 41 include individual light detectors that are selectively responsive only to the first light for the detector of station 40, and to the second light for the detector of station 41. In this case, the two signals on conductors 44 and 45 also appear during this time common interval. Comparator 33 may or may not include a latch means (now shown) to latch the magnitudes of these two signals 44, 45 as the signal comparison is made. The two stations 40, 41 may also operate during two different time intervals. In this case, the light detector that is within each of the two stations 40, 41 is rendered operative only during the period of operation of that respective station 40, 41. Since interference is precluded by providing different time periods of operation for the two light detectors, the two light detectors may be of a relatively wide color response. The two electrical signals on conductors 44 and 45 also appear during these two different time intervals, and signal comparator 33 in this case includes a latch means (not shown) that operates to latch the magnitudes of these two signals 44, 45 in order to enable a comparison to be made after expiration of the later or second time interval. Note that in accordance with an important feature of the invention, each individual light source and its mating light detector are located on the same side of collect tube 22.

In accordance with an important feature of this invention, the signal comparison provided at 33 is a comparison, such as a ratio calculation, that takes advantage of the fact that red light reflection increases and green light reflection decreases as the concentration of red blood cells increases.

Figure 5:
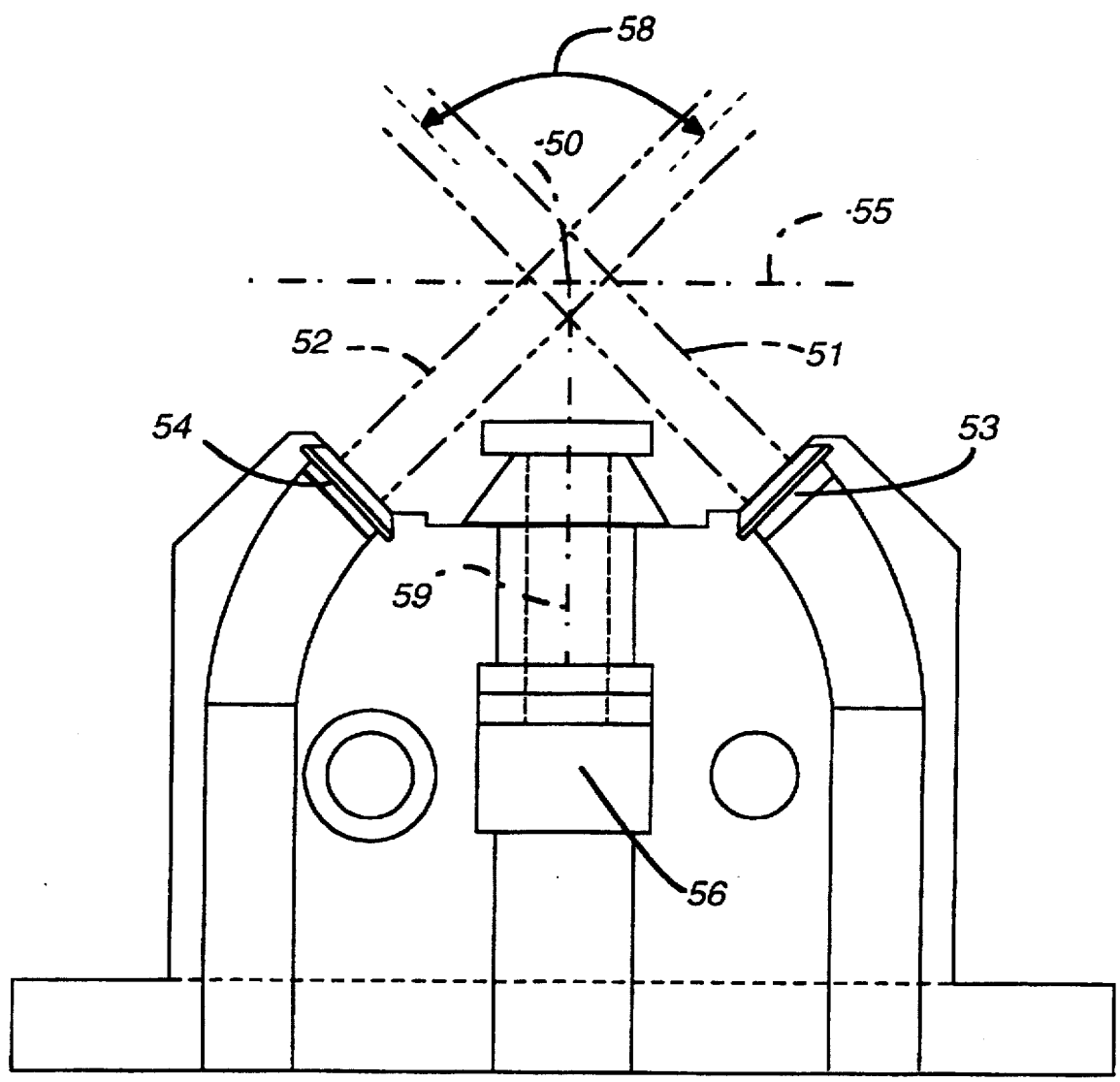
FIG. 5 shows a preferred embodiment of the invention wherein blood component flow takes place perpendicular to the plane of the figure, wherein red light and green light are projected at an angle of about 45 degrees to the collect tube-axis of a collect tube, and wherein a single photodetector views the collect tube along an angle generally 90 degrees to the collect tube-axis.

FIG. 5 shows a preferred embodiment of the invention wherein blood component flow takes place through a three dimensional volume 50 that is defined by the intersection of a red-light beam 52 and a green-light beam 51. The direction of blood component flow relative to the plane of FIG. 5 is not critical. For example, flow may be perpendicular to the plane of FIG. 5, flow may be in the plane of FIG. 5, or flow may take place at an angle to the plane of FIG. 5. That is, area 50 represents a generally spherical volume that carries the blood component flow to be monitored, for example this flow may take place within a circular cross section, visually transparent, collect tube as previously described.

The two linear, rod-shaped beams 51 and 52 of FIG. 5 generally designate a beam of green light that is emitted from a green LED 53, and a beam of red light 52 that is emitted from a red LED 54. Beams 51, 52 are, for example, circular in cross section. In this embodiment of the invention, light beams 51, 52 are directed at an angle of about 45 degrees to a horizontal reference axis 55 that extends in the plane of FIG. 5, i.e. beams 51, 52 define an included angle 58 of about 90 degrees.

A photosensor 56 that is responsive to both green light reflection and red light reflection is positioned to view volume 50 and the red light and green light that is reflected therefrom. This reflection takes place along a photosensor view axis 59 that extends downward at about 90 degrees to reference axis 55, i.e. photosensor view axis 59 generally bisects angle 58. While not critical to the invention, sensor 56 comprises a photodiode, having a size of about 2.92 mm.

LEDs 53, 54 and photosensor 56 are all located in a common plane that includes volume 50, i.e., for example, they may be located in the plane of FIG. 5, or they may be located in a common plane that is inclined to the plane of FIG. 5. In any case, as will be appreciated, the detailed construction and arrangement of FIG. 5 provides a number of mechanical or physical support surfaces and the like. In operation, photosensor 56 operates to detect red light and green light that is reflected off of these various surfaces as well as from the blood components that are flowing through volume 50.

In accordance with a feature of the invention, LEDs 53, 54 are pulsed off and then on at the rate of about 2 Khz, with a generally equal off/on duty cycle. This pulse energization of LEDs 53, 54 is time-staggered such that one LED is on during the time interval that the other LED is off.

The two output signals that are provided by photosensor 56, i.e. a red light reflection output during one time interval, and a green light reflection output during a second time interval, are now processed by a signal comparator such as 33 of FIGS. 3 and 4, in accordance with FIG. 2. With this FIG. 5 construction and arrangement, the hematocrit is about 1 percent when this ratio equals about 1.5. Using the unique ratio calculation of this invention accommodates changes in surface finish of the apparatus, changes in cleanliness, changes in alignment and physical orientation of the apparatus parts, optoelectronic component changes, etc., all of which may occur between testing runs and with the passage of time.

Figure 6:
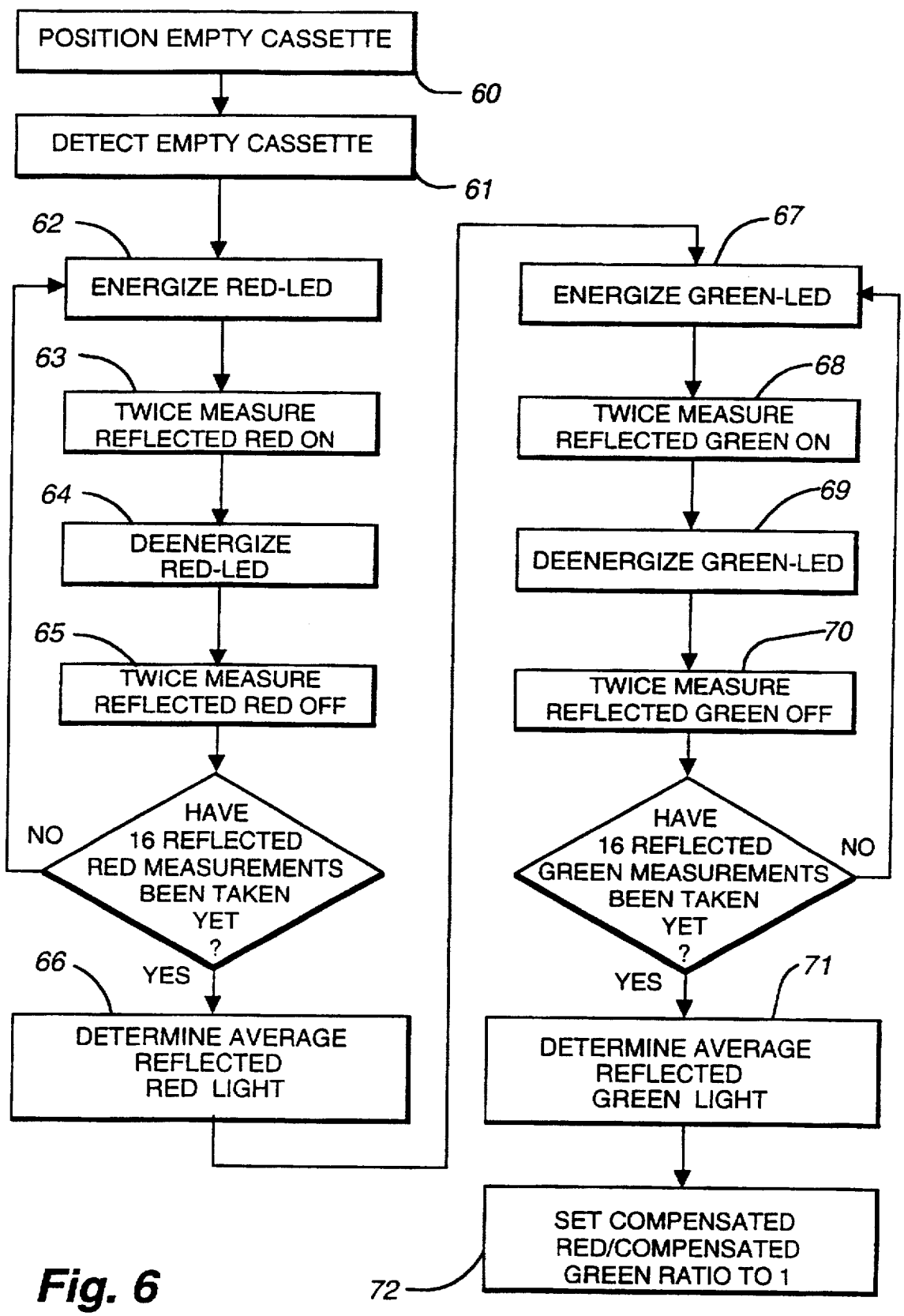
FIG. 6 is a flowchart showing of an initializing procedure for the apparatus of FIG. 5.

In order to initialize the apparatus of FIG. 5 the procedure shown in FIG. 6 is followed. At function 60, a dry, empty cassette is positioned in a red blood cell spillover detector 24 in which LEDs 53 and 54 are off. The blood separation system 20 of which the detector 24 is a part immediately and automatically detects the presence of an empty cassette (function 61) and is programmed to immediately proceed to perform a series of operations to adjust a compensated red/compensated green ratio to 1 prior to introduction of blood into the cassette.

Initially, the red LED 53 is energized for eight cycles with an LED which functions at 2000 cycles/second, as shown at function 62. During each of the eight cycles energizing red LED 53, two sample measurements are taken and stored, and represent reflected red light on values, as shown at function 63. Thereafter, red LED 53 is deenergized (function 64), during which time two sample measurements are taken and designated reflected red light off values, as shown at function 65. The functions 62, 63, 64 and 65 are repeated seven more times, that is, until sixteen reflected red light on measurements are collected and sixteen reflected red light off measurements are collected. Thereafter, the average reflected red light is determined by averaging the sixteen reflected red light on measurements, averaging the sixteen reflected red light off measurements, and subtracting the average reflected red light off from the average reflected red light on, as shown at function 66.

The green LED 54 is then energized for eight cycles with an LED which also functions at 2000 cycles/second, as shown at function 67. During each of the eight cycles energizing green LED 54, two sample measurements are taken and stored, and represent reflected green light on values, as shown at function 68. Thereafter, green LED 54 is deenergized (function 69), during which time two sample measurements are taken and designated reflected green light off values, as shown at function 70. The functions 67, 68, 69 and 70 are repeated seven more times, that is, until sixteen reflected green light on measurements are collected and sixteen reflected green light off measurements are collected. Thereafter, the average reflected green light is determined by averaging the sixteen reflected green light on measurements, averaging the sixteen reflected green light off measurements, and subtracting the average reflected green light off from the average reflected green light on (function 71).

The FIG. 6 initializing procedure is completed at function 72 by setting the calculated red/green ratio to be equal to the value "one", which may be accomplished by adjusting the energizing current to the green LEDs 54. If a value of "one" cannot be achieved with such an adjustment, the system is placed in an alarm condition. Note that it is not critical to the invention whether the average reflected red light is determined (steps 62–66) before or after the average reflected green light is determined (steps 67–71). In addition, it should be understood that before step 72 is performed and the compensated red/compensated green ratio is set to one, as described above, multiple repetitions of steps 62–71 may be performed, thereby providing additional data for the average reflected light values and the red/green ratio. Furthermore, it should also be understood that while in the presently preferred embodiment, a specific number of measurements and cycle frequencies are disclosed, the number, frequency, and pattern of measurements and cycles may be varied.

Blood then is introduced into the cassette, and as it flows therethrough, reflected red light and reflected green light are repeatedly measured as described in steps 62–71. After each pair of average reflected red light and reflected green light values are obtained (steps 66 and 71), a ratio of reflected red to reflected green is obtained. If the ratio of reflected red to reflected green reaches or exceeds predetermined limits, than a spillover condition is indicated.

Figure 7:
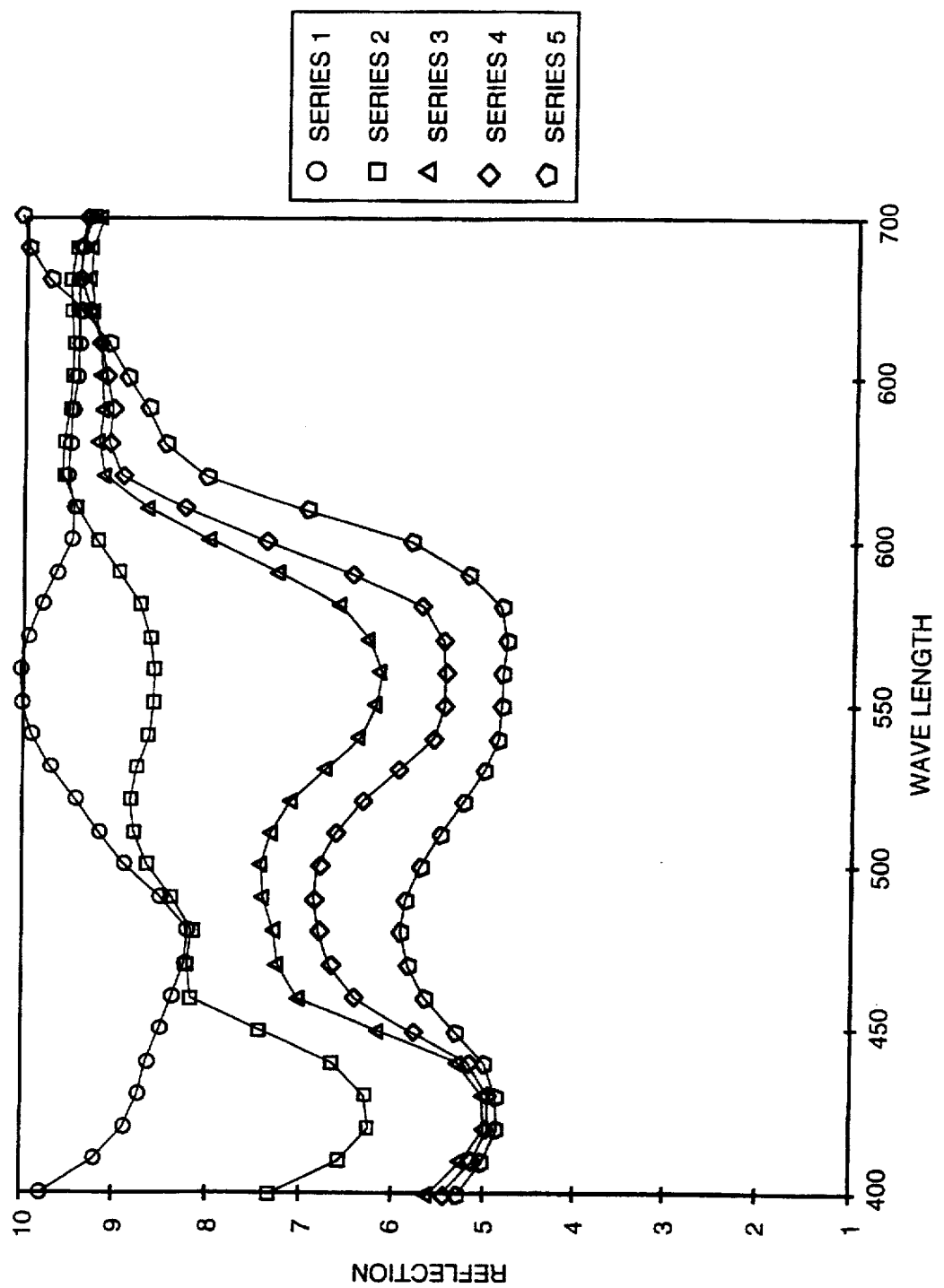
FIG. 7 is a graph which contains a multiplicity of curves each of which represent changes in light reflection measured at wavelengths of from 400 to 700 nm incident upon a blood sample from a donor having a relatively high concentration of platelets, wherein the hematocrit of the samples range from a zero hematocrit (Series 1) to 3% hematocrit (Series 5).

Referring now to FIG. 7, changes in reflection of light of wavelengths of from 400 to 700 nm incident upon a blood sample from a donor having a relatively high concentration of platelets are plotted. The blood sample tested in Series 1 had a zero hematocrit (hct), the sample tested in Series 2 had a 0.1% hct, the sample tested in Series 3 had a 0.5% hct, the sample tested in Series 4 had a 1% hct and the sample tested in Series 5 had a 3% hct. The approximate ratios of reflected red light of approximately 700 nm to reflected green light of approximately 550 nm from FIG. 7 are summarized in Table I.

TABLE I

| SERIES | HEMATOCRIT | REFLECTED RED / REFLECTED GREEN | RATIO |
|---|---|---|---|
| 1 | 0% | 9.3 / 10 | 0.9 |
| 2 | 0.1% | 9.3 / 8.6 | 1.1 |
| 3 | 0.5% | 9.2 / 6.2 | 1.5 |
| 4 | 1% | 9.3 / 5.4 | 1.7 |
| 5 | 3% | 10 / 4.9 | 2.0 |

As can been seen clearly in Table I, there is a trend of increase in the ratio of reflected red to reflected green light from a zero hematocrit to a hematocrit of 3%, and even a differentiation between a zero hematocrit sample and a sample having a hemotocrit of 0.1%.

Figure 8:
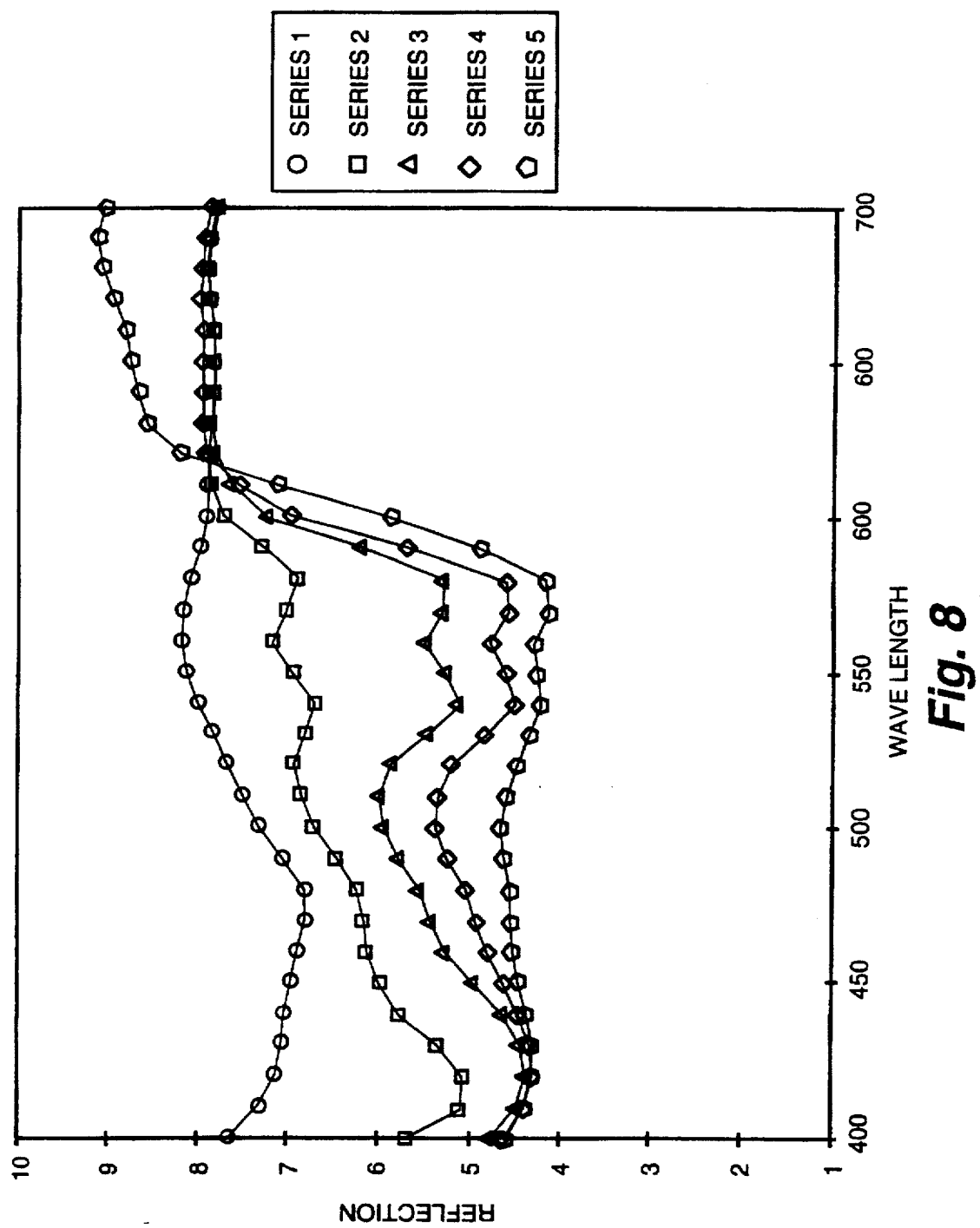
FIG. 8 is a graph which contains a multiplicity of curves similar to that of FIG. 7, in which the blood sample is from a donor having a normal concentration of platelets.

Referring now to FIG. 8, changes in reflection of light of wavelengths of from 400 to 700 nm incident upon a blood sample from a donor having a relatively normal concentration of platelets are plotted for samples in which hematocrit is varied in a similar manner to the Series illustrated in FIG. 7. The approximate ratios of reflected red light of approximately 700 nm to reflected green light of approximately 550 nm from FIG. 8 are summarized in Table II.

TABLE II

| SERIES | HEMATOCRIT | REFLECTED RED / REFLECTED GREEN | RATIO |
|---|---|---|---|
| 1 | 0% | 7.8 / 8.1 | 1.0 |
| 2 | 0.1% | 8.0 / 6.9 | 1.2 |
| 3 | 0.5% | 7.9 / 5.3 | 1.5 |
| 4 | 1% | 8.0 / 4.7 | 1.7 |
| 5 | 3% | 9.0 / 4.3 | 2.1 |

As can been seen clearly in Table II, there is a trend of increase in the ratio of reflected red to reflected green light from a zero hematocrit to a hematocrit of 3% which is substantially the same as measured for the blood sample having a high concentration of platelets. Once again, there is a differentiation between a zero hematocrit sample and a sample having a hematocrit of 0.1%.

Referring now to FIG. 9, changes in reflection of light of wavelengths of from 400 to 700 nm incident upon a blood sample from a donor having a relatively low concentration of platelets are plotted for samples in which hematocrit is varied in a similar manner to the Series illustrated in FIGS. 7 and 8. The approximate ratios of reflected red light of approximately 700 nm to reflected green light of approximately 550 nm from FIG. 9 are summarized in Table III.

TABLE III

| SERIES | HEMATOCRIT | REFLECTED RED / REFLECTED GREEN | RATIO |
|---|---|---|---|
| 1 | 0% | 7.7 / 7.7 | 1.0 |
| 2 | 0.1% | 7.7 / 7.0 | 1.1 |
| 3 | 0.5% | 7.7 / 5.3 | 1.4 |
| 4 | 1% | 7.7 / 4.6 | 1.7 |
| 5 | 3% | 8.8 / 4.3 | 2.0 |

As can been seen clearly in Table III, there is a trend of increase in the ratio of reflected red to reflected green light from a zero hematocrit to a hematocrit of 3% which is substantially the same as measured for the blood samples having high and normal concentrations of platelets. Once again, there is a differentiation between a zero hematocrit sample and a sample having to a hematocrit of 0.1%.

A review of the data shown in FIG. 6 and summarized in Table I in combination with the data shown in FIG. 7 and summarized in Table II indicates that blood samples having higher platelet concentrations may be differentiated from blood samples having lower platelet concentrations using the technique of the present invention. For example, green light reflection of blood samples having a zero hematocrit (Series 1) decreases from a high platelet concentration value of approximately 10 to a normal platelet concentration value of approximately 8. Also by way of example, green light reflection of blood samples having a 1% hematocrit (Series 4) decreases from a high platelet concentration value of approximately 5.6 to a normal platelet concentration value of approximately 4.5. Thus, platelets have been found to affect reflection of light as a function of concentration and/or density.

In yet another embodiment, polyvinyl cassettes used to evaluate blood samples using the technique of the present invention were treated with hot stamp foil rectangle approximately ½" by 1" of one of three colors—black, gray (foil No. LT12106) and white (No. CC11206). Reflectivity of green and red light as described above was measured on blood samples having differing hematocrit values. The results are summarized below in Table IV.

TABLE IV

| HEMA-TOCRIT | REFLECTED RED / REFLECTED GREEN | | | RATIO | | |
|---|---|---|---|---|---|---|
| | w/black back-ground | w/gray back-ground | w/white back-ground | w/black back-ground | w/gray back-ground | w/white back-ground |
| no cassette | 5/20 | | | | | |
| empty cassette | 185/136 | 636/292 | 944/886 | | | |
| 0% | 52/24 | 775/349 | 1018/942 | 2.2 | 2.2 | 1.1 |
| 0.5% | 60/18 | 752/187 | 985/646 | 3.3 | 4.0 | 1.5 |
| 1% | 69/15 | 725/156 | 936/480 | 4.6 | 4.6 | 2.0 |
| 2% | 90/14 | 705/119 | 888/390 | 6.4 | 5.9 | 2.3 |
| 3% | 128/20 | 687/105 | 844/339 | 6.4 | 6.5 | 2.5 |

A review of the data shown in Table IV indicates how the empty cassettes marked with selected black, gray and white foil have distinguishing reflectivity. This varying reflectivity may be used, for example, to indicate the nature of the disposable set mounted to the blood separator, or may be indicative of the blood components to be collected, or both. The data shown in Table IV also appears to indicate that regardless of the presence of the foils identified above and attached to the cassettes tested, there remains a trend of increasing ratio of red reflectivity to green reflectivity in blood samples, as hematocrit increases in the blood samples.

The present invention has been described in detail while making reference to various embodiments thereof, including the preferred embodiment thereof. Since it is apparent that those skilled in the art to which this invention relates, will, upon learning of the invention, visualize yet other embodiments that are within the spirit and scope of the invention, the forgoing detailed description is not to be taken as a limitation on the spirit and scope of this invention.

What is claimed is:

1. Apparatus for monitoring a light transparent tube adapted to carry flow of a first blood component, and for detecting the undesirable presence or spillover of a second blood component into the tube flow, the apparatus comprising:

a first and a second light source physically located in relation to a side of the tube so that light emission from said first light source and from said second light source are directed toward said side of the tube, said first light source having a first wavelength that is selected to produce a first light reflection intensity from any second blood component that may be present in the tube flow, the first light reflection intensity increasing as a function of an increase in concentration of the second blood component in the tube flow, and said second light source having a second wavelength that is selected to produce a second light reflection intensity from any second blood component that may be present in the tube flow, the second light intensity decreasing as a function of an increase in the concentration of the second blood component in the tube flow;

a light intensity responsive photosensor operable to detect said first light reflection intensity and said second light reflection intensity; and an output device controlled by said photosensor.

2. The apparatus of claim 1 wherein said output device operates to detect a ratio of said first light reflection intensity to said second light reflection intensity.

3. The apparatus of claim 2 wherein said first light source and said second light source are pulse energized during a first time interval and a second time interval, respectively, and said photosensor operates to detect said first light reflection intensity during said first time interval and to detect said second light reflection intensity during said second time interval.

4. The apparatus of claim 1 wherein the second blood component is red blood cells, wherein said first light source is a red light source, and wherein said second light source is a green light source.

5. The apparatus of claim 4 wherein said output device detects a ratio of said first light reflection intensity to said second light reflection intensity.

6. The apparatus of claim 5 wherein the first blood component comprises platelets.

7. The apparatus of claim 6 wherein said first light source and said second light source are energized during a first time interval and a second time interval, respectively, wherein said photosensor operates to detect said first light reflection intensity during said first time interval and to detect said second light reflection intensity during said second time interval, and wherein said first light source and said second light source are pulse energized.

8. The apparatus of claim 1 wherein said first light source, said second light source, and said photosensor are all physically located adjacent to the same side of the tube, to facilitate the physical loading of the tube onto the apparatus.

9. The apparatus of claim 8 wherein said output device detects a ratio of said first light reflection intensity to said second light reflection intensity.

10. A method of monitoring a non-red blood cell and light transparent tube and detecting the quantity of red blood cells that may be flowing in the tube, comprising the steps of:

directing red light toward a side of the tube;

directing green light toward a side of the tube;

detecting a red light reflection intensity from red blood cells that may be flowing within the tube;

detecting a green light reflection intensity from red blood cells that may be flowing within the tube; and providing an output by detecting a ratio of said red light reflection intensity to said green light reflection intensity.

11. The method of claim 10 wherein said step of providing an output includes the steps of;

providing a threshold value, and comparing said ratio to said threshold value.

12. The method of claim 10 wherein said step of directing said red light toward the tube and said step of detecting said red light reflection intensity occur during a first time interval, and wherein said step of directing said green light toward the tube and said step of detecting said green light reflection intensity occur during a second time interval that is different than said first time interval.

13. The method of claim 12 wherein said step of provided an output includes the steps of:
providing a threshold value, and
comparing said ratio to said threshold value.

14. The method of claim 10 wherein said side of the tube toward which red light is directed, and said side of the tube toward which green light is directed, comprise a common side of the tube.

15. The method of claim 10 wherein said side of the tube toward which red light is directed, and said side of the tube toward which green light is directed, comprise opposite sides of the tube.

16. A method sensing red blood cell spillover into a non-red blood tube, comprising the steps of:
providing a light transparent empty tube;
providing a photosensor to view an external portion of one side of said tube;
determining a first output of said photosensor when said photosensor views said external portion of said empty tube;
providing a red light source that is located to illuminate said external portion of said one side of said tube with red light when said red light source is energized;
providing a green light source that is located to illuminate said external portion of said one side of said tube with green light when said green light source is energized;
determining a second output of said photosensor while said photosensor views said external portion of said empty tube, and while only said red light source is energized;
determining a third output of said photosensor while said photosensor views said external portion of said empty tube, and while only said green light source is energized;
establishing a compensated red photosensor output by subtracting said first output for said second output;
establishing a compensated green photosensor output by subtracting said first output for said third output;
providing ratio determining means;
initializing said ratio determining means by utilizing said ratio determining means to establish a ratio equals one output from said ratio determining means when said ratio determining means determines the ratio of said compensated green photosensor output to said compensated red photosensor output;
filling said tube with a non-red blood cell sample that is normally devoid of red blood cells;
energizing only said green light source, to thereby direct green light toward said external portion of said filled tube;
determining a fourth output of said photosensor as said photosensor views green light that is reflected from said non-red blood sample within said filled tube while only said green light source is energized;
energizing only said red light source, to thereby direct red light toward said external portion of said filled tube;
determining a fifth output of said photosensor as said photosensor views red light that is reflected from said non-red blood sample within said filled tube while only said red light source is energized; and
utilizing said initialized ratio determining means to provide a red blood cell spillover output as a function of a ratio of said fifth output and said fourth output.

17. Apparatus for continuously monitoring the flow of a non-red blood cell blood component for the occurrence of a spillover of red blood cells, comprising:
a generally elongated and light transparent tube for carrying the flow of a non-red blood cell blood component, said tube having a generally elongated tube axis;
a red light source located to one side of the tube and positioned to direct a beam of red light at an angle of about 45 degrees to said tube axis, and toward an external portion of said one side of the tube, when said red light source is energized;
a green light source located to said one side of the tube and positioned to direct a beam of green light at an angle of about 45 degrees to said tube axis, and toward said external portion of said one side of the tube when said red light source is energized;
a photodetector that is responsive to red light reflection and to green light reflection, said photodetector being located to said one side of the tube and positioned to view said external portion of said one side of the tube along a view axis that extends generally normal to said tube axis;
energizing means for alternately pulse energizing said red light source during a first time interval and said green light source during a second time interval;
ratio determining means responsive to a red light reflection output from said photodetector during said first time interval, and to a green light reflection output from said photodetector during said second time interval; and
red blood spillover output means controlled by said ratio determining means as a function of a ratio of said red light reflection output to said green light reflection output.

18. The apparatus of claim 17 wherein said energizing means provides generally equal time periods of pulse energizing of said red light source and said green light source.

19. The apparatus of claim 18 wherein said red light source and said green light source comprise light emitting diodes.

20. The apparatus of claim 19 wherein said light emitting diodes are energized at a frequency of about 2 Khz.

21. The apparatus of claim 20 wherein the tube is a component of a disposable set and wherein the photosensor is further operable to detect a third reflection intensity and a fourth reflection intensity before a blood component is carried in said tube and to determine a configuration of the disposable set based on said third and fourth reflection intensities.

* * * * *